United States Patent [19]

Knobs et al.

[11] Patent Number: 4,797,412
[45] Date of Patent: Jan. 10, 1989

[54] FUNGICIDAL SUBSTITUTED CYCLOPROPYL OXIME ETHERS

[75] Inventors: Hans-Joachim Knops, Monheim, Fed. Rep. of Germany; Karl Steinbeck, Kansas City, Mo.; Karl H. Büchel, Burscheid, Fed. Rep. of Germany; Wilhelm Brandes, Leichlingen, Fed. Rep. of Germany; Paul Reinecke, Leverkusen, Fed. Rep. of Germany

[73] Assignee: Bayer Aktiengesellschaft, Leverkusen, Fed. Rep. of Germany

[21] Appl. No.: 942,154

[22] Filed: Dec. 16, 1986

[30] Foreign Application Priority Data

Dec. 19, 1985 [DE] Fed. Rep. of Germany ....... 3545085

[51] Int. Cl.$^4$ ................. A01N 43/653; C07D 249/08
[52] U.S. Cl. ..................................... 514/383; 514/184; 514/399; 548/101; 548/262; 548/341
[58] Field of Search ................ 548/101, 262; 514/184, 514/383

[56] References Cited

U.S. PATENT DOCUMENTS

| | | | |
|---|---|---|---|
| 4,264,772 | 4/1981 | Krämer et al. | 548/262 |
| 4,293,715 | 10/1981 | Kramer | 548/262 |
| 4,549,900 | 10/1985 | Kramer et al. | 548/262 |
| 4,603,140 | 1/1986 | Rerser et al. | 548/262 |

FOREIGN PATENT DOCUMENTS

| | | | |
|---|---|---|---|
| 0044993 | 2/1982 | European Pat. Off. | 548/262 |
| 0158299 | 10/1984 | European Pat. Off. | 248/262 |
| 2816817 | 10/1979 | Fed. Rep. of Germany | 548/262 |

OTHER PUBLICATIONS

Scherm et al, "Substituted Phenylethylimidazols, etc.", CA 104:68864f (1986).

*Primary Examiner*—Richard L. Raymond
*Assistant Examiner*—Patricia L. Morris
*Attorney, Agent, or Firm*—Sprung, Horn, Kramer & Woods

[57] ABSTRACT

Fungicidally active substituted cyclopropyl oxime ethers of the formula

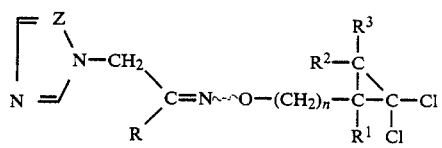

in which
Z represents a nitrogen atom or the CH group,
R represents a optionally substituted phenyl, or represents the grouping

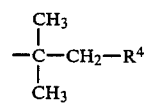

in which
$R^4$ represents hydrogen or optionally substituted phenyl,
$R^1$, $R^2$ and $R^3$ independently of one another represent hydrogen, methyl or chlorine and
n represents an integer from 1 to 6,
or addition products thereof with acids or metal salts.

7 Claims, No Drawings

FUNGICIDAL SUBSTITUTED CYCLOPROPYL OXIME ETHERS

The present invention relates to new substituted cyclopropyl oxime ethers, a process for their preparation and their use as fungicides.

It has already been disclosed that certain oximino-triazolyl-ethanes and salts thereof have good fungicidal properties (compare U.S. Pat. No. 4,264,772) Thus, for example, 1-(2,4-dichlorophenyl)-1-(2,4-dichlorobenzyloximino)-2-(1,2,4-triazol-1-yl)-ethane nitrate and 1-(2,4-dichlorophenyl)-1-(methoximino)-2-(1,2,4-triazol-1-yl)-ethane nitrate can be used for combating fungi. However, the action of these compounds is not always completely satisfactory, especially when low amounts are applied.

New substituted cyclopropyl oxime ethers of the formula

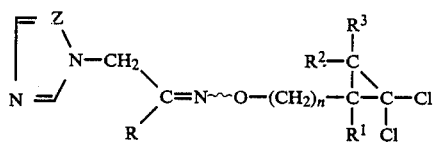

in which

Z represents a nitrogen atom or the CH group,

R represents optionally substituted phenyl, or represents the grouping

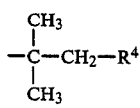

in which $R^4$ represents hydrogen or optionally substituted phenyl, $R^1$, $R^2$ and $R^3$ independently of one another represent hydrogen, methyl or chlorine and n represents an integer from 1 to 6, and acid addition salts and metal salt complexes thereof have been found.

The compounds of the formula (I) can exist in the syn or anti form; they are chiefly obtained as mixtures of the two forms.

It has furthermore been found that the substituted cyclopropyl oxime ethers of the formula (I) and acid addition salts and metal salt complexes thereof are obtained by a process in which oximes of the formula

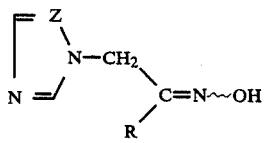

in which Z and R have the above-mentioned meaning, are reacted with cyclopropane derivatives of the formula

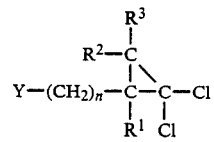

in which $R^1$, $R^2$, $R^3$ and n have the above-mentioned meaning and

Y represents halogen or p-methyl-phenyl-sulphonyloxy, if appropriate in the presence of a strong base and in the presence of a diluent, and, if appropriate, an acid or a metal salt is added onto the compounds of the formula (I) thus obtained.

Finally, it has been found that the new substituted cyclopropyl oxime ethers of the formula (I) and acid addition salts and metal salt complexes thereof are distinguished by very good fungicidal properties.

Surprisingly, the substances according to the invention have a better fungicidal activity than the oximino-triazolyl-ethanes 1-(2,4-dichlorophenyl)-1-(2,4-dichlorobenzyloximino)-2-(1,2,4-triazol-1-yl)-ethane nitrate and 1-(2,4-dichlorophenyl)-1-(methoximino)-2-(1,2,4-triazol-1-yl)-ethane nitrate which are known from the prior art and are closely related compounds structurally and from the point of view of their action.

Formula (I) provides a general definition of the substituted cyclopropyl oxime ethers according to the invention. Preferred compounds of the formula (I) are those in which Z represents a nitrogen atom or the CH group, R represents the groupings

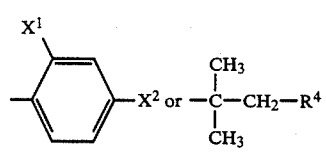

in which $X^1$ and $X^2$ are identical or different and represent hydrogen, halogen or halogenoalkyl, $X^1$ and $X^2$ not simultaneously representing hydrogen, and $R^4$ represents hydrogen or phenyl which is optionally mono-, di- or trisubstituted by identical or different substituents, preferred substituents which may be mentioned being halogen and alkyl with one to four carbon atoms, $R^1$, $R^2$ and $R^3$ independently of one another represent hydrogen, methyl or chlorine and n represents an integer from 1 to 6.

Particularly preferred compounds of the formula (I) are those in which

Z represents a nitrogen atom or the CH group,

R represents the groupings

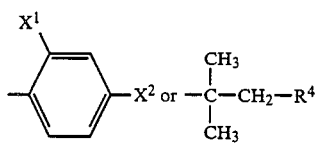

in which

X¹ and X² are identical or different and represent hydrogen, fluorine, chlorine, bromine or halogenoalkyl with one or two carbon atoms and one to five identical or different halogen atoms, such as, preferably, fluorine and chlorine, X¹ and X² not simultaneously representing hydrogen, and R⁴ represents hydrogen or phenyl which is optionally mono- or disubstituted by identical or different substituents, substituents which may be mentioned being chlorine, fluorine and methyl, R¹, R² and R³ independently of one another represent hydrogen, methyl or chlorine and n represents an integer from 1 to 4.

Addition salts of acids and those substituted cyclopropyl oxime ethers of the formula (I), in which Z, R, R¹, R², R³ and n have the meanings which have already been mentioned as preferred for these substituents and the index n, are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acid, such as, for example, p-toluenesulphonic acid and 1,5-naphthalene disulphonic acid.

Addition products of salts of metals of main group II to IV and subgroup I and II and IV to VIII of the periodic table of the elements and those compounds of the formula (I), in which Z, R, R¹, R², R³ and n have the meanings which have already been mentioned as preferred for these substituents and the index n, are furthermore preferred compounds according to the invention.

Salts of copper, zinc, manganese, magnesium, tin, iron and nickel are particularly preferred here. Possible anions of these salts are those which are derived from those acids which lead to physiologically acceptable addition products. Particularly preferred acids of this type are, in this connection, the hydrogen halide acids, such as, for example, hydrochloric acid and hydrobromic acid, and furthermore phosphoric acid, nitric acid and sulphuric acid.

If, for example, 1-(2,4-dichlorophenyl)-1-oximino-2-(1,2,4-triazol-1-yl)-ethane and 2,2-dichlorocyclopropylmethyl bromide are used as starting substances, the course of the reaction in the process according to the invention can be represented by the following equation:

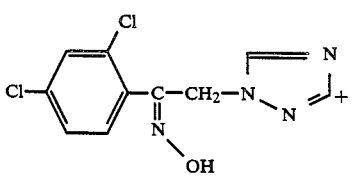

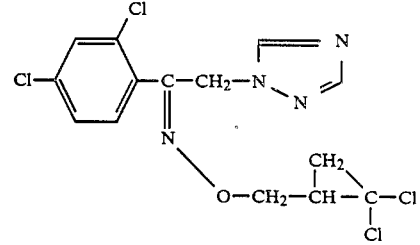

Formula (II) provides a general definition of the oximes required as starting substances in carrying out the process according to the invention. In this formula, Z and R preferably have those meanings which have already been mentioned as preferred for these radicals in connection with the description of the substances of the formula (I) according to the invention.

The oximes of the formula (II) are known (compare DE-OS (German Published Specification) No. 2,431,401, U.S. Pat. Nos. 4,327,104, 4,264,772, DE-OS (German Published Specification) No. 2,824,394 and European Patent No. 0,094,572. They can be obtained by a process in which azolyl ketones of the formula

in which

R has the abovementioned meaning and

Az represents 1,2,4-triazol-1-yl or imidazol-1-yl, are reacted with hydroxylamine in the presence of a solvent, preferably alcohols or aqueous alcohols, at temperatures between 20° C. and 100° C., preferably between 50° C. and 80° C. The hydroxylamine is thereby preferably employed in the form of its salts, in particular as the hydrochloride, in the presence of an acid-binding agent, such as, for example, sodium carbonate. The compounds of the formula (II) are isolated by a procedure in which the product formed during the reaction is worked up by customary methods after the solvent has been distilled off.

The azolyl ketones of the formula (IV) can be obtained by a process in which halogenoketones of the formula

in which

R has the above-mentioned meaning and

Y¹ represents chlorine or bromine, are reacted with 1,2,4-triazole or imidazole in the presence of a diluent, such as methyl ethyl ketone, and in the presence of an acid-binding agent, such as potassium carbonate, at temperatures between 20° C. and 150° C., preferably between 60° C. and 120° C.

Formula (III) provides a general definition of the cyclopropane derivatives also to be used as starting substances for the process according to the invention.

In this formula, $R^1$, $R^2$, $R^3$ and n preferably have those meanings which have already been mentioned as preferred for these radicals or this index in connection with the description of the substances of the formula (I) according to the invention. Y preferably represents chlorine, bromine or p-methyl-phenylsulphonyloxy (=tosyl).

The cyclopropane derivatives of the formula (III) are known in some cases (compare Liebigs Ann. Chem. 1979, p. 920 and Synthesis 1974, p. 274). They can be synthesized by processes which are known in principle. Thus, compounds of the formula (III) are obtained by a process in which allyl derivatives of the formula

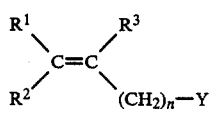

(VI)

in which $R^1$, $R^2$, $R^3$, Y and n have the above-mentioned meanings, are reacted with chloroform in the presence of triethylbenzylammonium chloride and aqueous sodium hydroxide solution at temperatures between 35° C. and 40° C.

The allyl derivatives of the formula (VI) are generally known compounds of organic chemistry.

Possible diluents for the reaction according to the invention are inert organic solvents. These include, preferably, ethers, such as tetrahydrofuran and dioxane; aromatic hydrocarbons, such as toluene and benzene; and hexamethyl-phosphoric acid triamide, acid amides, such as dimethylformamide, and sulphoxides, such as dimethyl sulphoxide.

If appropriate, the reaction according to the invention is carried out in the presence of a strong base. Strong bases include, preferably, alkali metal amides, hydrides, hydroxides and carbonates, such as, for example, sodium amide, carbonate, hydroxide or hydride and potassium amide, carbonate, hydroxide or hydride, and quaternary ammonium hydroxides and phosphonium hydroxides, such as, for example, tetramethylammonium hydroxide, benzyltrimethyl-ammonium hydroxide or dibenzyl-dimethyl-ammonium hydroxide and tetraphenylphosphonium hydroxide or methyltriphenylphosphonium hydroxide.

The reaction temperatures can be varied within a substantial range in the process according to the invention. The reaction is in general carried out between 0° C. and 150° C., preferably at room temperature. In individual cases, it is advantageous to carry out the reaction at the boiling point of the solvent, for example between 60° C. and 100° C.

In carrying out the process according to the invention, 1 to 3 mols of cyclopropane derivative of the formula (III) are employed per mol of oxime of the formula (II). The end products of the formula (I) are isolated in a known manner.

In a preferred embodiment of the process according to the invention, the reaction is carried out in a two-phase system, such as, for example, aqueous sodium hydroxide solution or potassium hydroxide solution/toluene, with the addition of 0.01-1 mol of a phase transfer catalyst, such as, for example, ammonium or phosphonium compounds.

All those acids which lead to physiologically acceptable salts are suitable for the preparation of acid addition salts of the compounds of the formula (I). Acids which can preferably be used are those which have already been mentioned as acids which are preferably to be added on in connection with the description of the substances according to the invention.

The acid addition salts of the compounds of the formula (I) can be prepared in a simple manner by customary salt formation methods. A procedure is in general followed in which a compound of the formula (I) is dissolved in a suitable inert diluent and an acid is then added. Isolation is effected in a known manner, for example by filtering off the salt and, if appropriate, by washing it with an inert organic solvent.

Salts of those metals which have already been mentioned as metal salts which are preferably to be added on in connection with the description of the substances according to the invention are preferably suitble for the preparation of metal salt complexes of the compounds of the formula (I).

The metal salt complexes of compounds of the formula (I) can be prepared in a simple manner by customary methods. A procedure is in general followed in which a metal salt is dissolved in alcohol, such as, for example, ethanol, and a compound of the formula (I) is then added. Isolation is likewise effected in a known manner, for example by filtering off the metal salt complex and, if appropriate, purifying it by recrystallization.

The active compounds according to the invention have a powerful microbicidal action and can be used in practice for combating undesirable micro-organisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as, for example, *Xanthomonas oryzae;* Pseudomonas species, such as, for example, *Pseudomonas lachrymans;* Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea;* (conidia form: Drechslera, syn: Helminthosporium); Cochliobolus species, such as, for example, *Cochliobolus sativus;* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fursarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Sphaerotheca species, such as *Sphaerotheca fuliginea* on cucumbers, and Uromyces species, such as *Uromyces appendiculatus.* The active compounds according to the invention are furthermore very suitable for combating Venturia species, such as *Venturia inaequalis* on apples, and cereal diseases, such as powdery mildew, Fusarium, *Septoria nodorum, Cochliobolus sativus* and *Pyrenophora teres.*

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lcithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The preparation and use of the active compounds according to the invention can be seen from the following examples.

PREPARATION EXAMPLE

Example 1

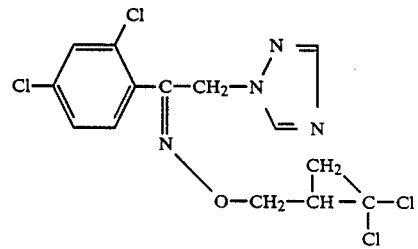

21.4 g (0.078 mol) of 1-(2,4-dichlorophenyl)-1-oximino-2-(1,2,4-triazol-1-yl)-ethane are mixed with 10.8 g (0.078 mol) of potassium carbonate and 100 ml of dimethylformamide and the mixture is warmed to 60° C. and added dropwise to a solution of 15.8 g (0.078 mol) of 2,2-dichlorocyclopropylmethyl bromide in 50 ml of dimethylformamide, while stirring. The reaction mixture is stirred at 60° C. for a further 12 hours. It is concentrated. After the residue has been stirred with water, the mixture is extracted three times with methylene chloride. The organic phase is washed with water, dried and concentrated. The residue which remains is purified by chromatography over silica gel with chloroform as the mobile phase 13 g (43% of theory) of 1-(2,2-dichlorocyclopropyl-methoximino)-1-(2,4-dichlorophenyl)-2-(1,2,4-triazol-1-yl)-ethane of refractive index $n_D^{22}=1.5647$ are obtained.

PREPARATION OF THE STARTING SUBSTANCES

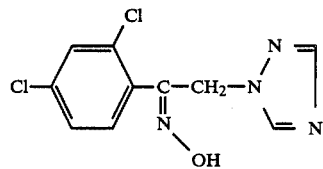

106.8 g (0.44 mol) of 1-(2,4-dichlorophenyl)-2-(1,2,4-triazol-1-yl)-1-ethanone are dissolved in 780 ml of ethanol, 48 g of hydroxylammonium nydrochloride are added and the mixture is heated under reflux for five hours. Thereafter, 1000 ml of water are added and the reaction mixture is filtered. 51 g (45% of theory) of 1-(2,4-dichlorophenyl)-1-oximino-2-(1,2,4-triazol-1-yl)-ethane of melting point 165°–170° C. are obtained.

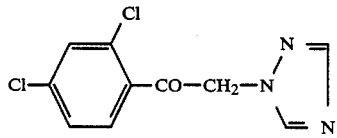

269 g (1 mol) of ω-bromo-2,4-dichloroacetophenone are dissolved in 250 ml of acetonitrile. This solution is added dropwise to a suspension, boiling under reflux, of 69 g (1 mol) of 1,2,4-triazole and 150 g of potassium carbonate in 2 l of acetonitrile. After the mixture has been heated under reflux for 20 hours, the cooled suspension is filtered, the filtrate is freed from the solvent and the residue is taken up in ethyl acetate. The mixture is then washed with water, dried over sodium sulphate and freed from the solvent under reduced pressure. The residue crystallizes out when isopropanol is added. After recrystallization from ligroin/isopropanol, 154 g (60% of theory) of 1-(2,4-dichlorophenyl)-2-(1,2,4-triazol-1-yl)-1-ethanone of melting point 117° C. are obtained.

The following compounds of the formula

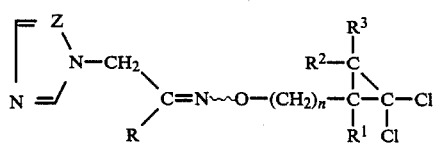

are obtained in a corresponding manner and in accordance with the process described:

| Exmp. No. | Z | R | n | R¹ | R² | R³ | Physical data |
|---|---|---|---|---|---|---|---|
| 2 | N | 2-Cl-phenyl | 1 | H | H | H | $n_D^{22}=$ 1.5707 |
| 3 | N | 2-Cl-phenyl | 1 | H | CH₃ | CH₃ | $n_D^{22}=$ 1.5613 |
| 4 | N | 2-Cl-phenyl | 1 | CH₃ | H | H | $n_D^{22}=$ 1.5544 |
| 5 | N | 2-Cl-phenyl | 2 | H | CH₃ | CH₃ | $n_D^{22}=$ 1.5594 |
| 6 | N | 2,4-Cl₂-phenyl | 1 | H | CH₃ | CH₃ | $n_D^{22}=$ 1.5576 |
| 7 | N | 2,4-Cl₂-phenyl | 1 | CH₃ | H | H | $n_D^{22}=$ 1.5803 syn. Form |
| 8 | N | 2,4-Cl₂-phenyl | 1 | CH₃ | H | H | $n_D^{22}=$ 1.5648 anti-Form |
| 9 | N | 2,4-Cl₂-phenyl | 2 | H | CH₃ | CH₃ | $n_D^{22}=$ 1.5504 |
| 10 | CH | 2,4-Cl₂-phenyl | 1 | H | H | H | $n_D^{22}=$ 1.5628 |
| 11 | CH | 2,4-Cl₂-phenyl | 2 | H | H | H | $n_D^{22}=$ 1.5855 |
| 12 | N | (CH₃)₃C— | 2 | H | H | H | b.p. 160° C./ 0.08 mbar |
| 13 | N | 2,4-Cl₂-phenyl | 2 | H | H | H | $n_D^{22}=$ 1.5874 |
| 14 | CH | 2,4-Cl₂-phenyl | 3 | H | H | H | *δ = 4.25 ppm (t, 2H) |
| 15 | CH | 2,4-Cl₂-phenyl | 4 | H | H | H | *δ = 4.25 ppm (t, 2H) |
| 16 | N | 2,4-Cl₂-phenyl | 3 | H | H | H | *δ = 4.30 ppm (t, 2H) |

-continued

| Exmp. No. | Z | R | n | R¹ | R² | R³ | Physical data |
|---|---|---|---|---|---|---|---|
| 17 | N | 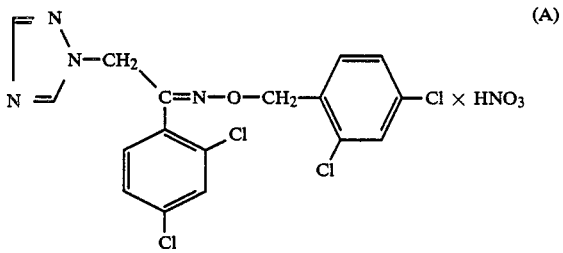 | 4 | H | H | H | *δ = 4.2 ppm (t, 2H) |

*¹H—NMR data (CDCl₃)
The δ-values represent the signals characterizing the —CH₂—O—N= group.

USE EXAMPLES

The substances shown below are employed as comparison compounds in the use examples which follow:

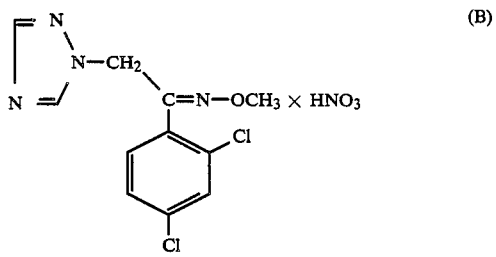

EXAMPLE A

Sphaerotheca test (cucumber)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, the substances according to the invention disclosed in Examples 1, 2, 6, 7 and 8 show a better activity than comparison substances (A) and (B).

EXAMPLE B

Uromyces test (dwarf bean)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous uredospore suspension of the bean rust causative organism (*Uromyces appendiculatus*) and remain in a dark humidity chamber at 20° to 22° C. and 100% relative atmospheric humidity for 1 day.

The plants are then placed in a greenhouse under intensive illumination at 20° to 22° C. and a relative atmospheric humidity of 70 to 80% for 9 days.

Evaluation is carried out 10 days after the inoculation.

In this test, the substances disclosed in Examples 1, 2, 4, 6, 7, 8 and 12 show a considerably better activity than comparison substance (A).

It will be understood that the specification and examples are illustrative but not limitative of the present invention and that other embodiments within the spirit and scope of the invention will suggest themselves to those skilled in the art.

We claim:

1. A substituted cyclopropyl oxime ether of the formula

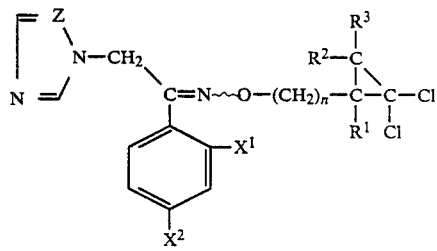

in which
z represents a nitrogen atom,
X¹ represents chlorine,
X² represents chlorine or hydrogen,
R¹, R² and R³ independently of one another represent hydrogen, methyl or chlorine and
n represents an integer from 1 to 4,
or an addition product thereof with an acid or metal salt.

2. A compound according to claim 1, wherein such compound is 1-(2,2-dichlorocyclopropylmethoximino)-1-(2,4-dichlorophenyl)-2-(1,2,4-triazol-1-yl)-ethane of the formula

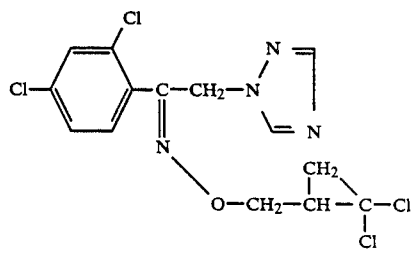

or an addition product thereof with an acid or metal salt.

3. A compound according to claim 1, wherein such compound is 1-(2,2-dichloro-3,3-dimethyl-cyclopropyl-methoximino)-1-(2,4-dichlorophenyl)-2-(1,2,4-triazol-1-yl)-ethane of the formula

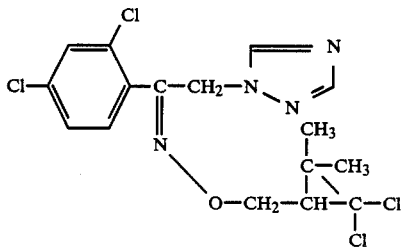

or an addition product thereof with an acid or metal salt.

4. A compound according to claim 1, wherein such compound is 1-(2,2-dichloro-1-methylcyclopropyl-methoximino)-1-(2,4-dichlorophenyl)-2-(1,2,4-triazol-1-yl)-ethane of the formula

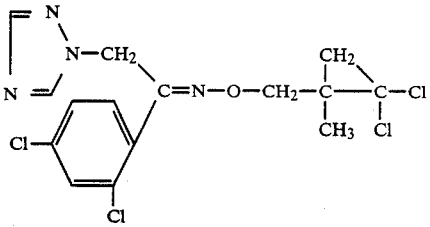

or an addition product thereof with an acid or metal salt.

5. A fungicidal composition comprising a fungicidally effective amount of a compound or addition product according to claim 1 and an inert diluent.

6. A method of combating fungi which comprises applying to such fungi or to a fungus habitat a fungicidally effective amount of a compound or addition product according to claim 1.

7. The method according to claim 6, wherein such compound is
1-(2,2-dichlorocyclopropylmethoximino)-1-(2,4-dichlorophenyl)-2-(1,2,4-triazol-1-yl)-ethane,
1-(2,2-dichloro-3,3-dimethyl-cyclopropylmethoximino)-1-(2,4-dichlorophenyl)-2-(1,2,4-triazol-1-yl)ethane, or
1-(2,2-dichloro-1-methylcyclopropyl-methoximino)-1-(2,4-dichlorophenyl)-2-(1,2,4-triazol-1-yl)-ethane,
or an addition product thereof with an acid or metal salt.

* * * * *